(12) United States Patent
Katschnig et al.

(10) Patent No.: US 6,524,539 B1
(45) Date of Patent: Feb. 25, 2003

(54) MICROWAVE STERILIZATION DEVICE

(75) Inventors: Helmut Katschnig, Burggasse 108, A-8750 Judenburg (AT); Wolfgang Stegmueller, St. Peter/Judenburg (AT); Ernst Gruber, Judenburg (AT)

(73) Assignee: Helmut Katschnig, Judenburg (AT)

( * ) Notice: Subject to any disclaimer, the term of this patent is extended or adjusted under 35 U.S.C. 154(b) by 0 days.

(21) Appl. No.: 09/677,687

(22) Filed: Oct. 2, 2000

(51) Int. Cl.[7] ................................. B01J 19/08
(52) U.S. Cl. ................ 422/186.07; 422/302; 422/295
(58) Field of Search ............. 422/186.07, 302, 422/295

(56) References Cited

U.S. PATENT DOCUMENTS

| | | | | |
|---|---|---|---|---|
| 4,406,861 A | * | 9/1983 | Beauvais et al. | ........... 422/302 |
| 5,407,641 A | * | 4/1995 | Katschnig | ................... 422/295 |
| 5,593,649 A | * | 1/1997 | Fisher et al. | ................. 422/295 |

FOREIGN PATENT DOCUMENTS

| | | |
|---|---|---|
| EP | 0 287 549 B1 | 3/1988 |
| EP | 0 483 104 B1 | 10/1991 |
| WO | WO 86/02842 | 5/1986 |
| WO | WO 90/15515 | 12/1990 |

OTHER PUBLICATIONS

*English Abstract of EP 0 483 104 B1.
*English Abstract of EP 0 287 549 B1.
*English Abstract of WO 90/15515.

* cited by examiner

*Primary Examiner*—Kishor Mayekar
(74) *Attorney, Agent, or Firm*—Reed Smith LLP

(57) ABSTRACT

Installation for the drying, heating, sterilization or disinfection of dry, moist or wet materials or materials in a moist environment and of liquids, particularly waste which may be infected, e.g., medical waste, in which the materials to be treated are introduced into a microwave-permeable vessel in a pressure-proof treatment space which can be acted upon by microwaves and sealed in a pressure-tight manner, wherein a plurality of magnetrons are coupled into the resonant space forming the treatment space in such a way that microwave dead spaces are prevented, wherein the physical parameters in the device are monitored and utilized for controlling the installation, and wherein added units are also provided for influencing the course of the process.

17 Claims, 4 Drawing Sheets

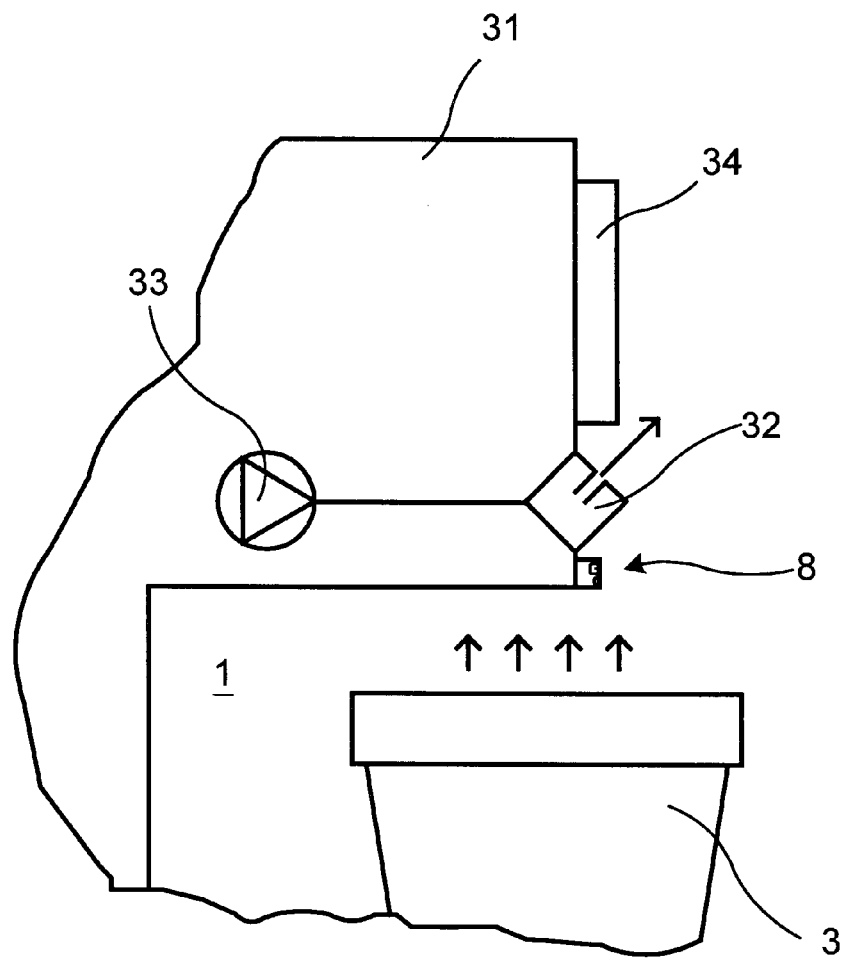
F I G. 6

MICROWAVE STERILIZATION DEVICE

The invention is directed to a n apparatus for the drying, heating, sterilization and/or disinfection of dry, moist or wet materials or materials in a moist environment and of liquids, particularly waste which may be infected, e.g., medical waste, in which the materials to be treated are introduced into a microwave-permeable vessel in a pressure-proof treatment space which can be acted upon by microwaves and sealed in a pressure-tight manner, wherein a plurality of magnetrons are coupled into the resonant space forming the treatment space in such a way that microwave dead spaces are prevented, wherein the physical parameters in the device are monitored and utilized, when appropriate, for controlling the installation, and wherein added units are also provided for influencing the course of the process, as well as to processes for pasteurization, disinfection or sterilization of dry, moist, or wet materials or materials in a moist environment and of liquids.

BACKGROUND OF THE INVENTION

An installation of this kind is known, for example, from WO 86/02842 in which there is provided a cylindrical interior space which can withstand internal pressures of up to 5 atmospheres or a partial vacuum. The top of this cylindrical space can be closed by a cover. The magnetrons are provided at the bottom end face of the cylindrical vessel, this underside being closed by a microwave-permeable pressure-proof wall. In order to achieve the most uniform possible distribution of microwave energy in this known construction, the inner cylindrical chamber is suspended so as to be rotatable in order to achieve control of the irradiation density of the individual particles by way of the movement of this cylindrical chamber. Further, because of this construction, the chamber of the known arrangement can only be loaded or charged from the top, which can quickly lead to difficulties when larger quantities of material packed in a drum must be introduced into the vessel. Further, condensation water can form on the wall in this known construction during cooling and must be removed from the vessel.

Another installation of the type mentioned above which is known from EP 0 476 004 B1 is also provided with a cylindrical treatment chamber which can be closed at the top. This treatment chamber (referred to in this reference as a cavity resonator) is lined with a vessel 1 which can be closed so as to be gastight, and the magnetrons are coupled into the treatment space laterally and from the bottom end face. Due to the lining provided in this known construction, the distance of the interior space from the microwave generators is controlled in such a way that a corresponding energy density is also present in this outer area.

This known construction also has the disadvantage that it is chargeable from the top, which accordingly impedes loading. Further, as can be gathered from this reference, the device must be charged with decalcified water because calcium deposits would otherwise occur in the lining. The construction according to this reference is also capable of operating with overpressure or underpressure.

It is known from EP 0 287 549 B1, whose subject matter also refers back to an invention of the Applicant of the present application as co-inventor, to couple a plurality of magnetrons into a cavity resonator in such a way that microwave dead spaces are prevented, wherein the coupling in is carried out via waveguides. However, this known construction is not provided as an overpressure sterilizer.

EP 0 483 104 B1 also cites the present Applicant as co-inventor, wherein, in an installation according to the above-cited EP 0 287 549, a vessel containing infectious waste is introduced into the cavity resonator, that is, the treatment chamber, and this vessel can be closed by a cover so that it can serve as a collecting vessel for this infectious waste. A carrier with physical measurement sensors can be lowered into the vessel from the top through an opening in the cover of this vessel, and water can also be sprayed in via this carrier when the quantity of water or moisture contained in the infectious material is too small. According to the known construction, the quantity of water or moisture is determined by an appropriate weighing device, and the supply of water is controlled by means of a central control device which controls the microwave generators corresponding to the measured physical data.

It is the object of the present invention to provide an installation of the type mentioned above which has the advantages of the side-charging treatment chamber according to EP 483 104 A2 as well as the advantages of a pressure chamber and which can therefore be used as an autoclave.

SUMMARY OF THE INVENTION

According to the invention, this is accomplished in that the magnetrons are coupled into the treatment space in a pressure-tight manner via waveguides, known per se, this treatment space being provided with a side charging opening for introducing the microwave-permeable vessel while leaving a free space between the vessel and the inner wall of the treatment space, wherein the treatment space has a cylindrical or polygonal prismatic shape with vertically extending longitudinal axis, and wherein the devices for monitoring the physical parameters are arranged at carriers communicating with the interior of the vessel. In this way, the distance between the material to be treated and the microwave generators can be controlled via the waveguides and intermediate space remaining between the vessel and the inner wall of the treatment space in such a way that the entire interior of the vessel receives the full microwave output, so that the irradiated microwave energy is sufficient for generating the necessary steam to achieve the operating overpressure. Further, the side charging opening makes it possible for larger-volume vessels that would no longer be manageable in practice with out auxiliary equipment to be introduced into th e treatment s pace.

The charging opening can be advantageously produced by parts of the treatment chamber along an off-center plane extending parallel to the longitudinal axis of the treatment chamber, wherein the bottom wall and top wall are also divided. Accordingly, a portion of the top wall and also a portion of the bottom of the treatment chamber are divided, which considerably facilitates insertion of the vessel by auxiliary means such as a suitably constructed trolley, lift truck or the like. However, the charging opening can be made by cutting out the casing wall of the treatment chamber along two generatrices and parallel to the bottom wall and top wall, so that the entire bottom surface and top surface remain intact and the charging opening is provided only in the wall, which can be advantageous under certain circumstances for purposes of economizing on space.

For a particularly space-saving construction, a combination of wave trap, known per se, and seal, preferably a hose seal which can be acted upon by internal pressure, can be provided along the charging opening for tightly closing this opening by means of the associated closing part. This offers the possibility of a compact construction of the seal for preventing the escape of microwaves and pressure without impairing the free through-opening.

In order to ensure that the sterilizing/disinfecting process actually occurs at the correct temperature within the material and not only at the temperature of the interior space, a thermal sensor by which carriers communicating with the interior of the vessel can be introduced into the microwave-permeable vessel or a noncontacting thermal sensor connected with a control device having a reference value storage and a comparator for comparing with the determined actual value can be provided for determining the regulating variable for the output of the magnetrons. The temperature in the material can be detected in a much more direct manner in this way because the temperature is measured there and then, and the steam or compressed steam flowing out is measured inside the entire installation in the immediate vicinity of the material. In this way, it can also be ensured that the desired temperature is reliably maintained over the given period within the material. In addition, a pressure sensor extending outside of the microwave-permeable vessel into the interior of the resonant chamber can be connected with the comparator, so that the ratios in the area of the resonator chamber located outside of the vessel can also be determined.

In order to prevent condensation from forming on the wall of the resonant chamber in the event of temperature differences, the wall of the resonant chamber can be provided with a heating device. The output of the heating device can be regulated depending on the temperature prevailing in the vessel for a particularly exact control.

In order to make possible controlled cooling and a controlled pressure drop in the resonant chamber, magnetic or solenoid valves provided in the outlet lines can be connected with the control device.

Finally, the interior of the resonant chamber and/or of the pressure hose of the seal can be connected with a compressor and/or a pressure accumulator, so that it is possible to apply pressure to the resonant chamber without waiting for the required amount of steam to be formed. This has the advantage that the corresponding temperature within the liquid proceeds without evaporation of the same, wherein energy can also be spared insofar as less water needs to be evaporated to build up pressure due to the pressure which is introduced externally. Moreover, the pressure can be stored in the resonant chamber and used for the next application of pressure to the pressure seal.

In order to prevent hot steam from flowing against the operating and display devices when the treatment chamber is opened, a nozzle strip or flat nozzle can be provided along one of the free edges of the charging opening at a housing which encloses the treatment chamber in conventional manner for blowing out the compressed air transversely or diagonally relative to the direction of the rising steam.

Therefore, when suitably outfitted and controlled, an installation which is generally constructed in this way can also be used as a standard autoclave.

In an advantageous process for pasteurization, disinfection/sterilization of dry, moist, or wet materials or materials in a moist environment or of liquids by means of the installation according to the invention, the materials to be treated can be introduced into a microwave-permeable, heat-resistant vessel, this vessel can then be inserted into the resonant chamber and, where appropriate, water is added to this vessel, whereupon the resonant chamber is closed in a pressure-tight manner and the resonant chamber is subsequently acted upon by microwaves and the materials located therein are heated to the desired temperature accompanied by an increase in pressure in the resonant chamber, wherein the output of the magnetrons is regulated by measuring the temperature of the steam flowing out of the materials and the temperature and pressure are maintained over the desired treatment period corresponding to a preselected model.

Since the total amount of water used for steam generation is in the vessel or in the material to be sterilized, there is no need for a water supply outside of the vessel in the pressure space or, therefore, for decalcified water, because any occurring residue remains on the materials to be sterilized and disinfected and is removed along with the latter. However, the material to be treated can also be introduced into a microwave-permeable vessel in the resonant chamber and the latter can be closed in a pressure-tight manner, whereupon the material to be treated is acted upon by microwaves, wherein the heating of the material and accordingly also the degree of drying is monitored by measuring the temperature of the steam flowing out of the material, and, as the case may be, the course of pressure is controlled over the treatment period corresponding to a preselected model via the output of the magnetrons. In this way, with a pressure-tight, pressure-resistant inner vessel, the high temperature need only be applied within the vessel, wherein the steam flowing off in the resonant chamber is again heated within the resonant chamber by the coupled in microwaves so that contamination of the resonant chamber is prevented. Further, after the vessel which is filled with liquid has been introduced and heated by means of the microwaves, the temperature and the pressure inside the vessel are monitored and the pressure in the resonant chamber outside the vessel is maintained identical to the pressure inside the vessel by means of a pressure source, wherein the material is gradually cooled by means of a gradual reduction in pressure within the resonant chamber. This prevents a boiling delay or other foaming over or escape of the contents of the vessel into the resonant chamber.

Finally, after the end of the sterilization/disinfection cycle and reduction of pressure in the resonant chamber to atmospheric pressure, vacuum pressure is applied to the resonant chamber and, along with it, the vessel interior, so that the disinfected or sterilized material is quickly dried and utilized further in this dry form.

An embodiment example of the subject matter of the invention is shown in the drawing.

BRIEF DESCRIPTION OF THE DRAWINGS

FIG. 6 is a schematic side view showing the upper part of the overall installation in a section of the housing.

DETAILED DESCRIPTION OF THE INVENTION

Figure 1:
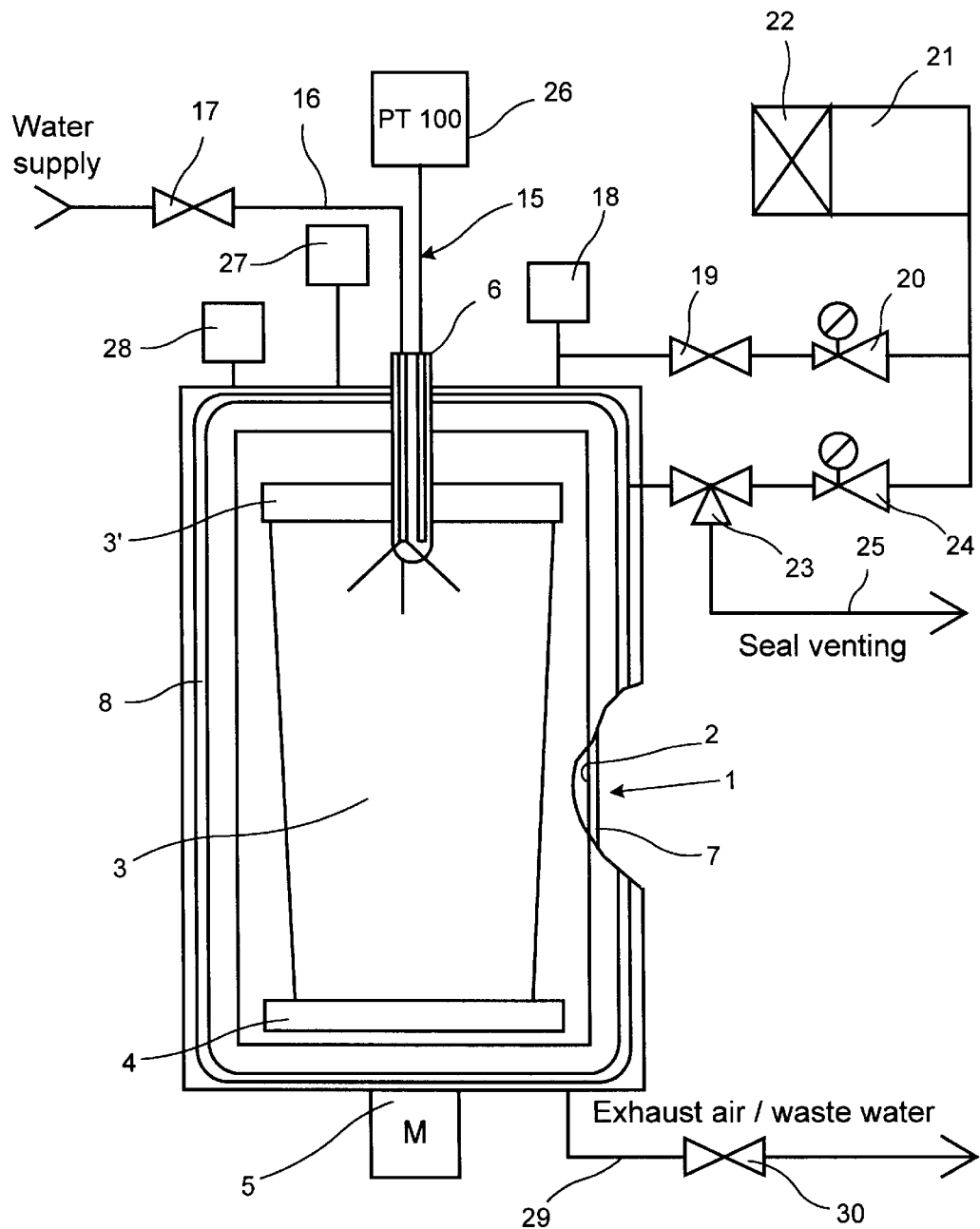
FIG. 1 shows schematically the overall installation with additional units connected thereto.
Figure 2:
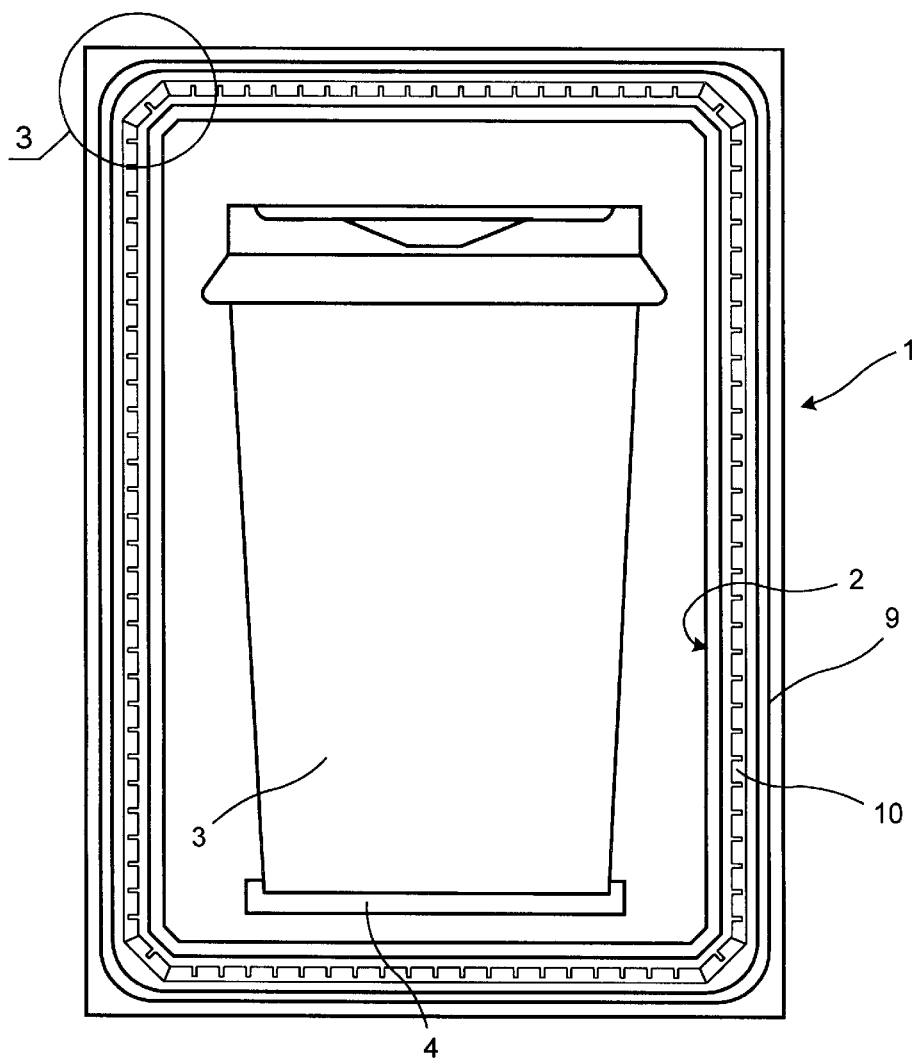
FIG. 2 is a front view, likewise schematic, showing the resonant chamber with open charging opening.
Figure 3:
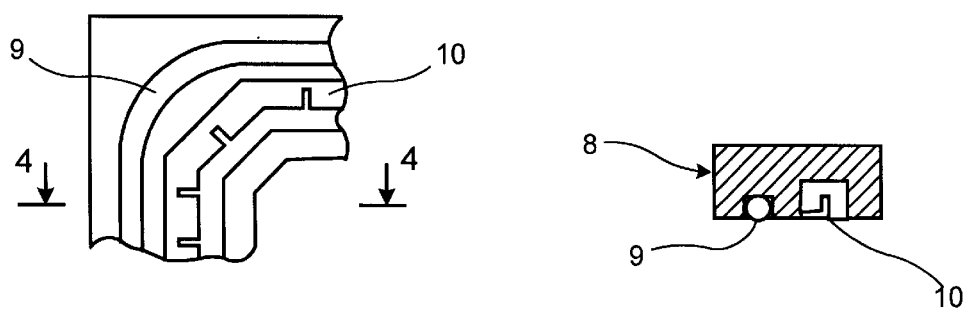
FIG. 3 shows a detail of section A from FIG. 2.
Figure 4:
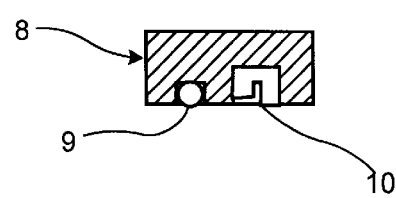
FIG. 4 shows a section along line IV—IV in FIG. 3.

A resonant chamber which is arranged in a conventional housing and defined by its inner wall 2 is designated by 1. A vessel 3 with a cover 3' can be inserted into this resonant chamber 1 on a rotary table 4 which communicates with a drive motor 5. This rotary table can also be a weighing device for determining the weight of the inserted filled vessel 3. The cover 3' has a central opening in which a carrier 6 for measurement devices can be made to communicate with the vessel interior.

The inner wall 2 of the resonant chamber 1 is provided with a heating device 7 which can be connected, in addition, to the microwave generators, if needed. The treatment space has a combination 8 of pressure seal 9 and wave trap 10 at the edge of the charging opening, wherein the pressure seal is formed by a pressure hose which can be acted upon by internal pressure after the doors have been closed and accordingly enables a reliable pressure-tight closure of the charging opening.

Figure 5:
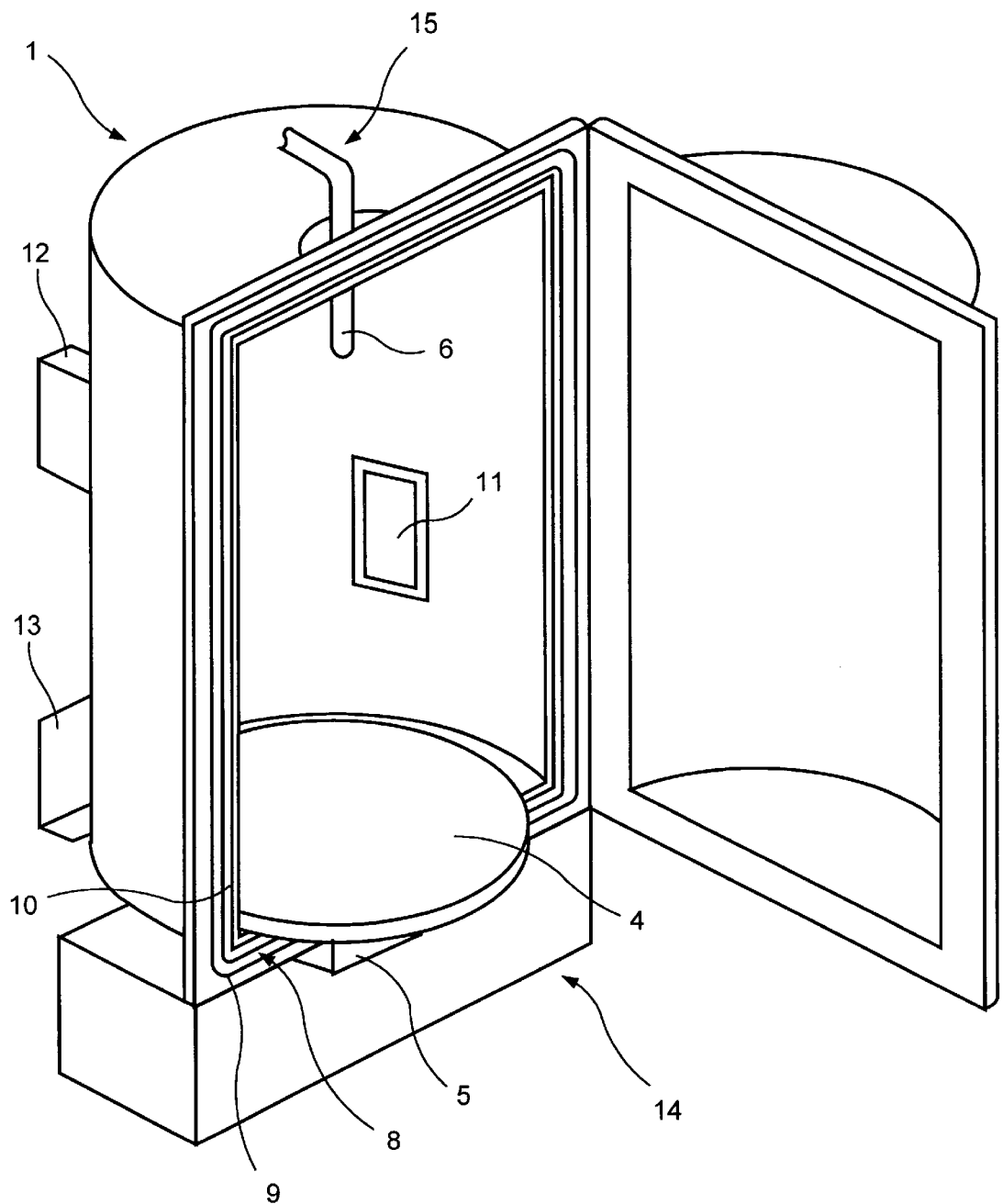
FIG. 5 shows the subject matter of the invention schematically.

FIG. 5 shows three magnetrons, designated by 11, 12, 13 which are coupled into the treatment space 1 via waveguides, known per se, wherein the exit window for the microwaves is closed in a pressure-tight manner with the inner wall 2.

As can also be seen from FIG. 5, the entire installation is supported on a carrying frame 14 in which the drive motor 5 for the rotary table and, if need be, also additional devices can be located.

The control lines leading out of the carrier 6 for measurement devices are designated by 15, wherein the carrier 6 for the measurement devices can contain a temperature sensor, a pressure sensor and possibly additional devices.

A feed line 16 which can be closed by means of a solenoid valve 17 opens into the carrier 6 for introducing water and - if necessary - additional treatment media, steam or other additions into the vessel 3.

A pressure sensor 18 which is separate from the carrier 6 is provided at the resonant chamber 1; a line having a solenoid valve 19 and a pressure reducer 20 leads from the feed line of the pressure sensor 18 to a pressure tank 21 which in turn is connected to a compressor 22. The pressure tank 21 and the compressor 22 are also connected with the interior of the pressure seal 9 via a line provided with a solenoid valve 23 and a pressure reducer 24. A ventilation line 25 for the seal 9 leads away from the solenoid valve 23. Gaseous media useful for treatment can also be introduced via the line provided with the solenoid valve 19.

The temperature measurement sensor provided in the carrier 6 for the measurement device is connected with a temperature measurement device 26.

A safety valve 27 and a vacuum pump 28 are also connected with the resonant chamber 1. An exhaust/drainage line 29 in which a solenoid valve 30 is connected also leads away from the bottom of the treatment space 1.

All magnetic devices and control devices as well as all measurement gauges are connected with a common control device, not shown, which compares the determined actual values with predetermined reference values and then controls the output of the magnetrons 11, 12 and 13 based on this comparison.

When a vessel 3 is sufficiently full of infectious waste for disposal, this vessel 3 is closed by the cover 3' and placed on the rotary table 4 of the treatment space 1. The kind of waste occurring is then entered into the control device, and the control device then calculates the amount of water required, if any, according to a predetermined algorithm based on the weight data detected via the rotary table 4. This algorithm and the calculation and control of the supply of water is described in detail in the above-cited EP 0 483 104 B1 which is expressly referred to and whose content is accordingly adopted in the present application by citation, i.e., EP 0483 104 B1 is incorporated herein by reference.

After the required quantity of water has been added via line 16 by controlling the solenoid valve 17 by means of the central control device and the door has been closed and pressure has been applied to the pressure seal 9, energy is applied to the magnetrons 11, 12, 13, so that the liquid in the vessel 3 is heated. If the temperature difference between the inner wall 2 of the resonator chamber 1 and the steam exiting from the vessel is too great, the heating device 7 is switched on so as to adapt the temperature of the wall to the temperature of the steam and prevent condensation. Due to the distance of the magnetrons from the treatment space and the coupling in via the waveguide, the steam in the treatment space 1 and accordingly also the inner wall 2 of the treatment space are heated to the extent that a separate heating of the inner wall 2 is almost unnecessary. By means of the temperature gauge located at the carrier 6 and arranged in the interior of the vessel 3 and by noncontacting thermal sensors, e.g., based on infrared operation, the temperature of the steam and therefore also the temperature of the material to be treated in the vessel 3 are measured, so that pressure is also measured indirectly. However, since the pressure measurement can be falsified because of the volatile substances present in the waste, the pressure in the treatment space 1 is also measured in parallel via the pressure sensor 18, so that it can also be determined whether the volatile substances are already evaporated and only pure steam is present inside the treatment space 1 or whether steam from volatile substances is still present therein. It is essential that the required temperature is maintained within the vessel 3 over a predetermined period of time because only in this way can it be ensured that all germs and spores will be reliably killed.

If necessary, water, additional treatment media, steam or other additions can also be supplied via line 16 during the treatment cycle.

At the conclusion of the treatment cycle, the pressure inside the treatment space 1 is let off via the solenoid valve 19 in a controlled manner by means of the pressure gauge 20 and a pressure vessel 21 in order to prevent boiling delays or other eruptions inside the vessel 3. If the material is still too moist at the end of the treatment period, vacuum drying can be carried out subsequently after normal pressure is reached via the vacuum pump 28, which does not entail problems insofar as the contents of the vessel 3 and the interior space of the treatment chamber 1 are sterile, obviating the use of sterile filters in the vacuum pump.

As soon as normal pressure has been restored in the treatment chamber 1, the pressure is relieved from the pressure hose of the seal 9 via the solenoid valve 23 and line 25, and the vessel 3, including the cover 3', is then removed from the treatment chamber 1 and the contents of the vessel 3 can be disposed of in the standard manner.

As is indicated in FIG. 6, the treatment chamber 1 is arranged in a conventional housing 31 in which all peripheral equipment such as computers and the like is also accommodated. A nozzle strip or flat nozzle 32 which is acted upon by a compressed air generator 33 is provided above the charging opening of the treatment chamber along the upper edge of the charging opening and can generate an air curtain in front of and above the charging opening in order to prevent hot steam from flowing against the operating and display devices 34 when opening after a treatment cycle. This nozzle strip or flat nozzle can also be arranged, in a manner not shown, along one of the other free edges of the charging opening, that is, at edges which are not covered by the opened charging doors when opened.

What is claimed is:

1. Apparatus for the drying, heating, sterilization and disinfection or a combination thereof comprising:
   a pressure-proof treatment chamber which can be acted upon by microwaves or having a pressure seal which is sealable in a pressure-tight manner;
   a plurality of magnetrons coupled into the treatment chamber and located in such a way that microwave dead spaces are prevented, said magnetrons being coupled into the treatment chamber in a pressure-tight manner via waveguides;
   a microwave-permeable vessel to be introduced into the treatment chamber via a side charging opening provided at the treatment chamber leaving a free space between the vessel and an inner wall of the treatment chamber;
   said opening being produced by dividing the treatment chamber along a plane that extends parallel to the longitudinal axis of the treatment chamber having a cylindrical or polygonal prismatic shape with a vertically extending longitudinal axis; and
   devices for monitoring the physical parameters in the apparatus device being arranged at carriers communicating with the interior of the vessel, which parameters are used, when appropriate, for controlling the apparatus.

2. The apparatus according to claim 1, wherein the charging opening is produced by parts of the treatment chamber along a plane which is off-center and which extends parallel to the longitudinal axis of the treatment chamber, wherein the bottom wall and top wall are also divided.

3. The apparatus according to claim 1, wherein the charging opening is made by cutting out a casing wall of the treatment chamber along two generatrices and parallel to a bottom wall and a top wall.

4. The apparatus according to claim 1, wherein a combination comprising wave trap and seal, which can be acted upon by internal pressure, is provided along the charging opening for tightly closing this opening by means of an associated closing part.

5. The apparatus according to claim 4 wherein the seal is a hose seal.

6. The apparatus according to claim 1, wherein a thermal sensor by which carriers communicating with the interior of the vessel can be introduced into the microwave-permeable vessel or a noncontacting thermal sensor connected with a control device having a reference value storage and a comparator for comparing with a determined actual value is provided for determining a regulating variable for an output of the magnetrons.

7. The apparatus according claim 1, wherein a pressure sensor extending outside of the microwave-permeable vessel into the interior of the treatment chamber is connected with the comparator.

8. The apparatus according to claim 1, wherein the wall of the treatment chamber is provided with a heating device.

9. The apparatus according to claim 8, wherein the output of the heating device can be regulated depending on the temperature prevailing in the vessel.

10. The apparatus according to claim 1, wherein solenoid valves provided in the outlet lines are connected with a control device.

11. The apparatus according to claim 1, wherein the interior of the treatment chamber or of the seal is connected with a compressor or a pressure accumulator.

12. The apparatus according to claim 1, wherein a nozzle strip or flat nozzle is provided along one of a free edges of the charging opening at a housing which encloses the treatment chamber configured for blowing out compressed air transversely or diagonally to the direction of the rising steam.

13. A process for pasteurization, disinfection, sterilization or a combination thereof comprising the steps of:
   introducing materials to be treated into a microwave-permeable, heat-resistant vessel;
   inserting the vessel into a treatment chamber;
   adding water or other treatment media where appropriate to the vessel,
   then closing the resonant treatment chamber in a pressure-tight manner;
   subsequently allowing the resonant treatment chamber to be acted upon by microwaves by a plurality of magnetrons coupled into the resonant treatment chamber and located in such a way that microwave dead spaces are prevented, said magnetrons being coupled into the resonant treatment chamber in a pressure-tight manner via waveguides;
   wherein at the step of inserting said vessel, said vessel is introduced into the resonant treatment chamber via a side charging opening provided at the resonant treatment chamber leaving a free space between the vessel and an inner wall of the resonant treatment chamber;
   heating the materials located therein to a desired temperature accompanied by an increase in pressure in the resonant treatment chamber;
   regulating an output of the magnetrons by measuring the temperature of steam flowing out of the materials; and
   maintaining the temperature of the materials, and pressure over a desired treatment period corresponding to a preselected model.

14. A process for the sterilization of liquids in pressure-proof closed vessels in an apparatus according to claim 13, comprising the steps of:
   after the vessel which is filled with liquid has been introduced and heated by means of the microwaves, monitoring the temperature and the pressure inside the vessel; and
   maintaining the pressure in the resonant treatment chamber outside the vessel identical to the pressure inside the vessel by a pressure source;
   gradually cooling the materials by a gradual reduction in pressure within the resonant treatment chamber.

15. The process according to claim 14, after the step of maintaining the temperature of the materials and pressure over a desired treatment period corresponding to a preselected model, further comprising the steps of:
   concluding a sterilization/disinfection cycle by reducing pressure in the resonant chamber treatment chamber to atmospheric pressure; and
   applying vacuum pressure to the resonant treatment chamber and, along with it, the vessel interior.

16. The process according to claim 14 wherein the step of maintaining the pressure in the resonant treatment chamber outside the vessel identical to the pressure inside the vessel by a pressure source is accomplished by introducing treatment gas as the pressure source.

17. The process according to claim 13 after the step of maintaining the temperature of the materials and pressure over a desired treatment period corresponding to a preselected model, further comprising the steps of:
   concluding a sterilization/disinfection cycle by reduction of pressure in the resonant treatment chamber to atmospheric pressure; and
   applying vacuum pressure to the resonant treatment chamber and, along with it, the vessel interior.

* * * * *